US00PP24003P2

(12) United States Plant Patent
Tsukahara

(10) Patent No.: US PP24,003 P2
(45) Date of Patent: Oct. 22, 2013

(54) ***CALIBRACHOA* PLANT NAMED 'CCZYE01-0'**

(50) Latin Name: ***Calibrachoa* sp.**
Varietal Denomination: CCZYE01-1

(75) Inventor: Jun Tsukahara, Yame (JP)

(73) Assignee: Daiichi Engei Co. Ltd (JP)

( * ) Notice: Subject to any disclaimer, the term of this patent is extended or adjusted under 35 U.S.C. 154(b) by 0 days.

(21) Appl. No.: 13/385,487

(22) Filed: Feb. 21, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Kent L Bell

(57) ABSTRACT

A new and distinct *Calibrachoa* cultivar named 'CCZYE01-0' is disclosed, characterized by large flower size and distinctive bright yellow flower color. The new variety is a *Calibrachoa*, normally produced as an ornamental outdoor garden or container plant.

2 Drawing Sheets

Latin name of the genus and species: *Calibrachoa* sp.
Variety denomination: 'CCZYE01-0'.

BACKGROUND OF THE INVENTION

The new *Calibrachoa* cultivar is a product of a planned breeding program conducted by the inventor, Jun Tsukahara in Yame, Fukuoka, Japan. The objective of the breeding program was to produce new *Calibrachoa* varieties for commercial ornamental applications. The cross resulting in this new variety was made during September 2007.

The seed parent is an unpatented, unnamed proprietary seedling variety of *Calibrachoa*, with a pale greenish yellow flower. The pollen parent is an unpatented, unnamed proprietary seedling variety of *Calibrachoa*, with a dark red flower. The new variety was discovered in May, 2008 by the inventor in a group of seedlings resulting from the 2007 crossing, in a research greenhouse in Yame, Fukuoka, Japan.

Asexual reproduction of the new cultivar 'CCZYE01-0' by tissue culture was first performed at a research greenhouse in Yame, Fukuoka, Japan in May, 2008. Subsequently, the new variety has been propagated by vegetative cuttings, and has shown that the unique features of this cultivar are stable and reproduced true to type in successive generations.

SUMMARY OF THE INVENTION

The cultivar 'CCZYE01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CCZYE01-0'. These characteristics in combination distinguish 'CCZYE01-0' as a new and distinct *Calibrachoa* cultivar:

1. Large flower size
2. Unique bright yellow flower color

PARENT COMPARISON

Plants of the new cultivar 'CCZYE01-0' are similar to plants of the seed parent, an unnamed proprietary seedling variety of *Calibrachoa*, with a pale greenish yellow flower, in most horticultural characteristics. However, plants of the new cultivar 'CCZYE01-0' produce larger flowers of a different color, as well as longer stems and narrower leaves.

Plants of the new cultivar 'CCZYE01-0' are similar to the plants of the pollen parent, an unpatented, unnamed proprietary seedling variety of *Calibrachoa*, with a dark red flower in most horticultural characteristics. However plants of the new cultivar 'CCZYE01-0' produce larger flowers of a different color, as well as shorter stems and wider leaves.

COMMERCIAL COMPARISON

Plants of the new cultivar 'CCZYE01-0' are best compared to the variety *Calibrachoa* 'SUNbelki', U.S. Plant Pat. No. 11,558. The two *Calibrachoa* varieties are similar in most horticultural characteristics, however, the new variety 'CCZYE01-0' differs in having an overall brighter yellow flower color and brighter yellow flower center.

BRIEF DESCRIPTION OF THE PHOTOGRAPHS

Figure 1:
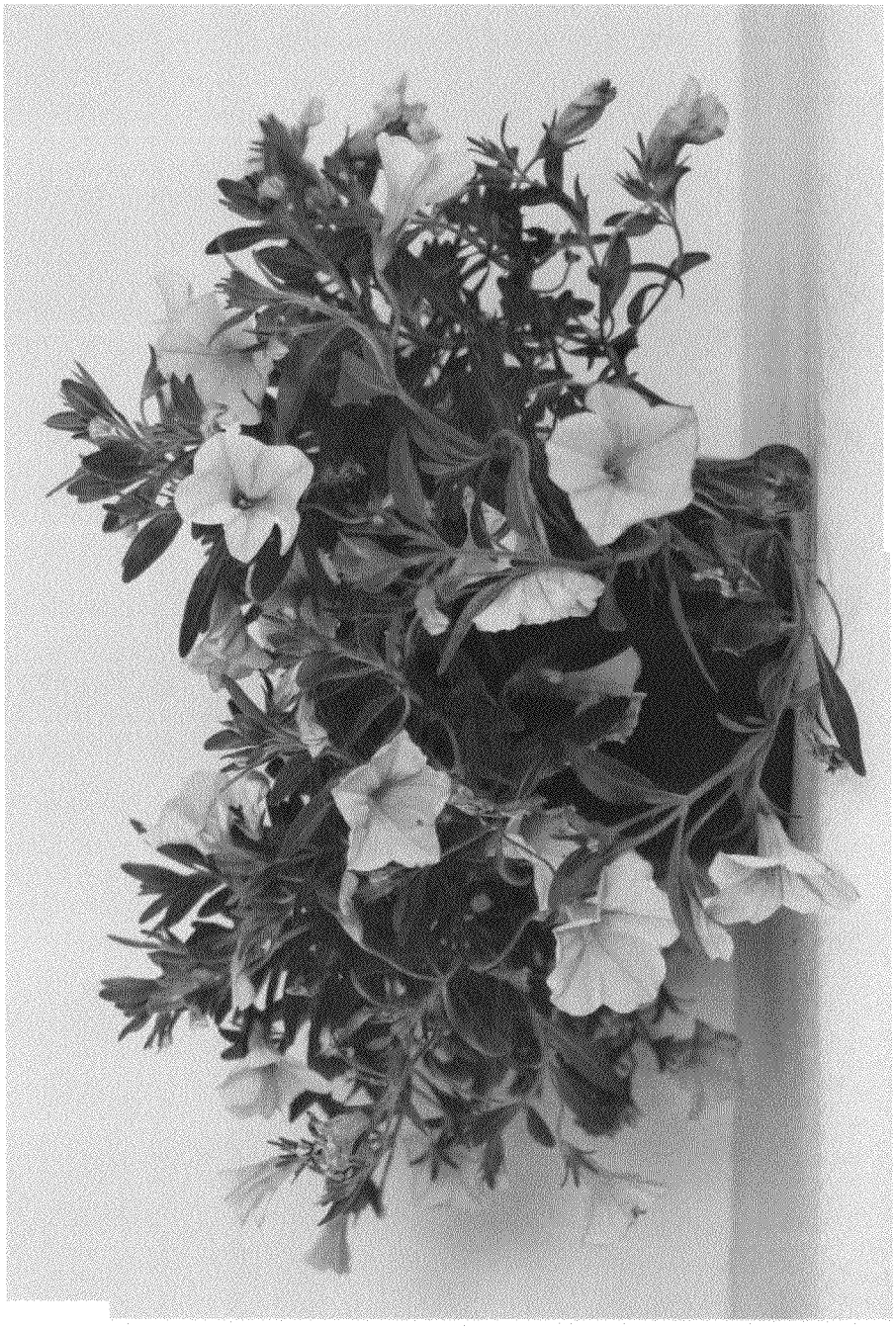

The accompanying photograph in FIG. 1 illustrates in full color a typical plant of 'CCZYE01-0' grown in a greenhouse, in a 6 inch pot.

Figure 2:
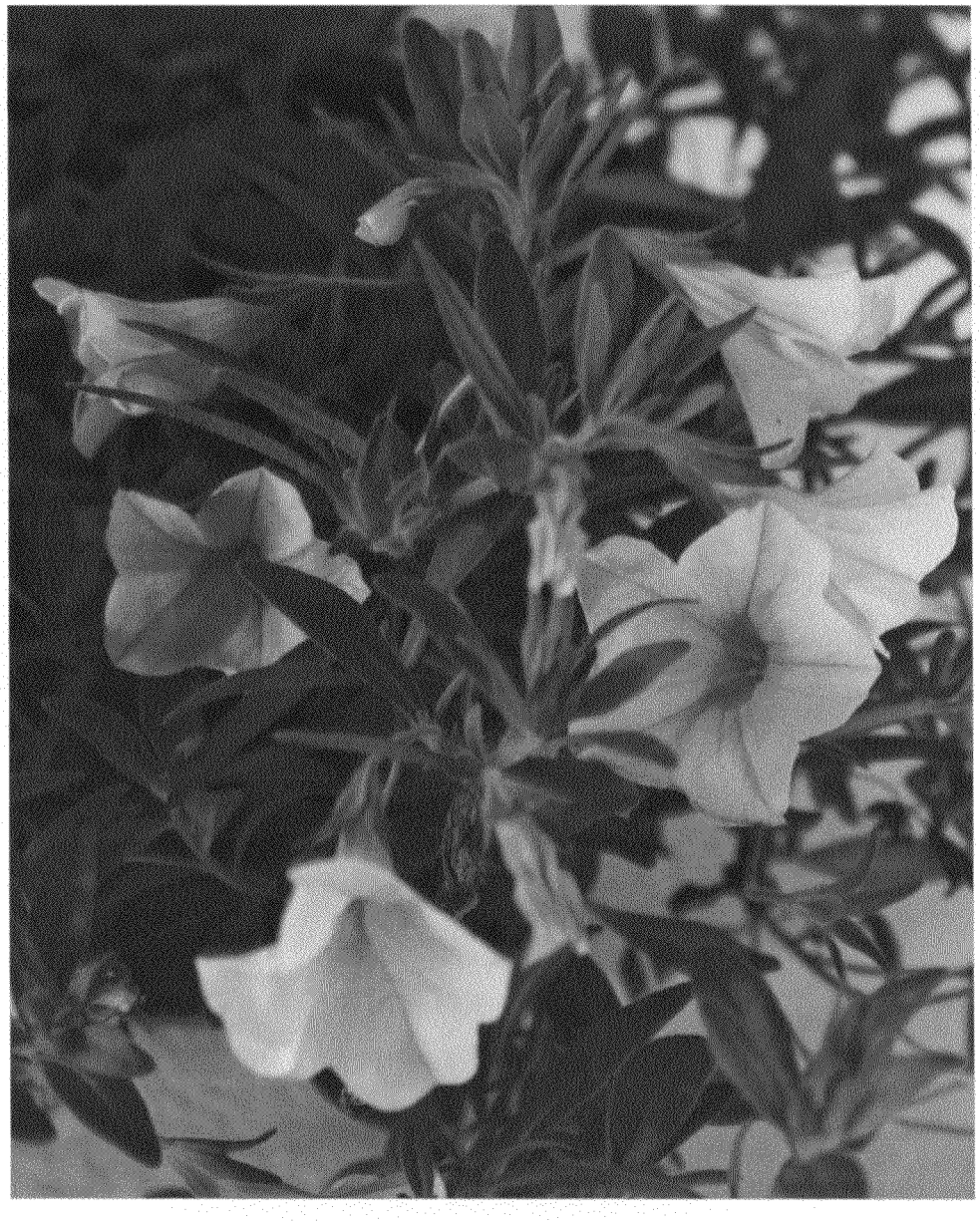

FIG. 2 illustrates in full color a close up of a typical bloom.

Age of the plant photographed is approximately 4 months from 5 rooted cuttings. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'CCZYE01-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.
Botanical classification: *Calibrachoa* sp. 'CCZYE01-0'.

PROPAGATION

Time to initiate roots: About to 10 to 12 days at approximately 25° C.
Root description: Fine, fibrous.

PLANT

Growth habit: Trailing.
Pot size of plant described: 6 inch.
Age of plant described: Approximately 4 months.
Height: Approximately 12 cm.
Plant spread: approximately 46 cm.
Growth rate: Rapid.
Branching characteristics: Moderately free branching.
Length of primary lateral branches: Approximately 12 cm.
Diameter of lateral branches: Approximately 0.3 cm.
Quantity of primary lateral branches: Approximately 20.
Characteristics of primary lateral branches:
*Form*.—Round.
*Color*.—Near RHS Green 143C.
*Texture*.—Pubescent.
*Strength*.—Strong.
Internode length: Average 0.5 to 1.8 cm.

FOLIAGE

Leaf:
*Arrangement*.—Opposite.
*Quantity*.—Approximately 18 per lateral branch.
*Average length*.—Average 3.5 cm.
*Average width*.—Average 1.1 cm.
*Shape of blade*.—Oblanceolate.
*Apex*.—Broadly acute to obtuse.
*Base*.—Acuminate.
*Margin*.—Entire.
*Texture of surfaces*.—Highly pubescent.
*Angle of attachment*.—75°.
*Aspect*.—Flat.
*Color*.—Young foliage upper side: Near RHS Green 137A. Young foliage under side: Near RHS Green 137C. Mature foliage upper side: Near RHS Green 137A. Mature foliage under side: Near RHS Green 137B.
*Venation*.—Type: Pinnate. Venation color upper side: Near RHS Yellow-Green 144A. Venation color under side: Near RHS Yellow-Green 144B.
*Petiole*.—Not Present.

FLOWER

Natural flowering season: All year round in moderate climates.
Days to flowering from rooted cutting: Approximately 4 weeks.
Inflorescence and flower type and habit: Terminal, Single, Salverform.
Rate of flower opening: 1 to 3 days from bud to fully opened flower.
Flower longevity on plant: About 3 to 6 days.
Approximate quantity of flowers per plant: 30-40 at 60 days old.
Persistent or self-cleaning: Self-cleaning.
Fragrance: Faint.
Bud:
*Shape*.—Tubular.
*Length*.—2.5 cm.
*Diameter*.—0.7 cm.
*Color*.—At proximal end Near RHS Yellow-Green N144C. At distal end Near RHS Green-Yellow 1B.
Flower size:
*Diameter*.—Average 4.0 cm.
*Length*.—Average 3.5 cm.
*Flower tube diameter at distal end*.—Average 1.25 cm.
*Flower tube diameter at proximal end*.—0.5 cm.
Petals:
*Length from throat*.—Average 2.1 cm.
*Width*.—Average 2.0 cm.
*Quantity*.—5 fused petals.
*Texture*.—Smooth.
*Apex*.—Broad acute.
*Margin*.—Entire.
*Color*.—When opening: Inner surface: Near RHS Yellow 12B. Outer surface: Near RHS Yellow 12C. Fully opened: Inner surface: Near RHS Yellow 9A. Outer surface: Near RHS Yellow 6D, faint, thin veins Yellow-Green 144B. Flower throat (inside): Near RHS Yellow 9B. Flower throat, vein: Near RHS Yellow-Green N144C. Flower tube (outside): Near RHS Yellow 3C. Flower tube, vein: Near RHS Yellow-Green N 144C. Petal color, fading to: Near RHS Yellow 10A.
Calyx/sepals:
*Quantity per flower*.—5.
*Shape*.—Lanceolate.
*Length*.—Approximately 1.4 cm.
*Width*.—Approximately 0.4 cm.
*Apex*.—Acute.
*Base*.—Fused.
*Margin*.—Entire.
*Texture*.—Pubescent.
*Color*.—Upper Surface: Near RHS Green 137A. Lower Surface: Near RHS Green 137B.
Peduncle:
*Length*.—Average 2.0 to 3.3 cm.
*Diameter*.—0.1 cm.
*Texture*.—Pubescent.
*Color*.—Near RHS Yellow-Green 144A.
*Orientation*.—Straight or slight undulation, 45° angle from stem.

REPRODUCTIVE ORGANS

Stamens:
*Number*.—5.
*Filament length*.—0.9 cm.
Anthers:
*Length*.—0.1 cm.
*Shape*.—Round.
*Color*.—Near RHS Yellow 7A.
*Pollen*.—Color: Near RHS Yellow 7A. Quantity: Moderate.
Pistil:
*Number*.—1.
*Length*.—0.8 cm.
*Style*.—Length: 1 cm. Color: Near RHS Green-Yellow 1B.
*Stigma*.—Shape: Bilobed. Color: Near RHS Yellow-Green 144B. Ovary Color: Near RHS Yellow-Green 144C.

OTHER CHARACTERISTICS

Seeds and fruits: Not observed.

Disease/pest resistance: Neither resistance nor susceptibility to pathogens and pests common to *Calibrachoa* have been observed.

Temperature tolerance: The new variety tolerates temperatures between 0 to 40° C.

What is claimed is:

1. A new and distinct cultivar of *Calibrachoa* plant named 'CCZYE01-0' as herein illustrated and described.

* * * * *